United States Patent [19]
Bessler

[11] Patent Number: 4,825,881
[45] Date of Patent: May 2, 1989

[54] APPLIANCE FOR ASSISTING IN WEIGHT CONTROL

[76] Inventor: Edward W. Bessler, 8 Rosemont Ave., Fort Mitchell, Ky. 41017

[21] Appl. No.: 168,466
[22] Filed: Mar. 15, 1988
[51] Int. Cl.$^4$ .............................................. A61F 5/56
[52] U.S. Cl. ................................................... 128/859
[58] Field of Search .............. 128/136, 132 R, 206.14, 128/206.25, 857, 858

[56] References Cited

U.S. PATENT DOCUMENTS

| | | | |
|---|---|---|---|
| 1,354,652 | 10/1920 | Jefferies | 128/136 |
| 1,775,718 | 9/1930 | Garvey | 128/136 |
| 4,050,457 | 9/1977 | Davidson | 128/132 R |
| 4,344,424 | 8/1982 | Barmby | 128/136 |
| 4,354,489 | 10/1982 | Riaboy | 128/206.14 |

FOREIGN PATENT DOCUMENTS 725336  1/1966  Canada .................................. 128/136

*Primary Examiner*—Robert A. Hafer
*Assistant Examiner*—Charles H. Sam
*Attorney, Agent, or Firm*—Irwin P. Garfinkle

[57] ABSTRACT

An appliance for inhibiting the intake of food is disclosed. The appliance comprises first and second spaced adhesive strips applied above and below the upper and lower lips of a user and interconnected by lines, which may be elastic, and which provide relatively normal movement of the mouth to permit normal speech, while at the same time inhibiting, but not totally preventing the intake of solids and liquids.

8 Claims, 1 Drawing Sheet

APPLIANCE FOR ASSISTING IN WEIGHT CONTROL

BACKGROUND OF THE INVENTION

This invention is directed to a simple device for aiding persons on weight reduction diets to control their food intake.

A search of the prior art reveals a number of appliances which are intended to assist in the control of food intake. For example, U.S. Pat. No. 3,224,442 to Stubbs, and the Brown et al, International Application Publication No. WO 86/01706 both show dental applianes worn in the mouth of the user for inhibiting eating. Stubbs U.S. Pat. No. 3,818,906 is a simpler device also worn in the user's mouth.

A patent of some relevance but not related to diet control is U.S. Pat. No. 3,677,250 which shows adhesive tape structure that could be adapted to my invention.

Unlike the known prior art devices, my invention uses a simple arrangement of two plastic strips adhered, respectively to the upper and lower lips of the user, and interconnected by food intake inhibiting elastic lines. In essence, my invention simulates the idea of sewing the user's lips together, but it does so in a manner which permits speech plus limited food and liquid intake, and is removable by the user at the user's will. Since the device is easily removable and disposable, the dieter is aid more in an emotional manner than by physical restraint, by providing a reminder of the dieter's own goals.

SUMMARY OF THE INVENTION

This invention is an appliance comprising first and second adhesive strips applied above and below the upper and lower lips of the user and interconnected by lines, which may be elastic, and which tend to inhibit food intake, while at the same time permitting normal mouth movements to permit speech and the limited intake of solids and liquids.

DESCRIPTION OF THE EXEMPLARY EMBODIMENTS

Figure 1:
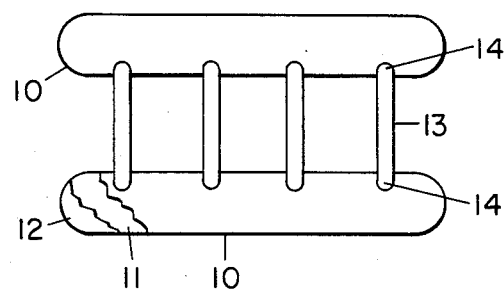
FIG. 1 is a top view of an exemplary embodiment of the invention.

Referring to FIG. 1, the appliance consists of two identical elongated and narrow strips of tape 10 to the bottom surface of which an adhesive 11 is applied. A conventional adhesive cover sheet 12 applied over the adhesive prevents premature sticking prior to use, and is easily peeled away. The two strips 10 which may be stamped from a sheet material, usually a plastic film, are interconnected by means of a plurality of parallel connecting lines 13, bonded to the plastic strips at spaced locations along the lengths thereof. The connecting lines may be formed of the same material as the strips, and preferably will be stretchable to permit movement of the user's lips for the purpose of enabling speech, and a limited amount of food and liquid intake. If the line 13 are not stretchable, then the device may be applied to the wearer's lips in such a manner as to provide some slack.

Figure 2:
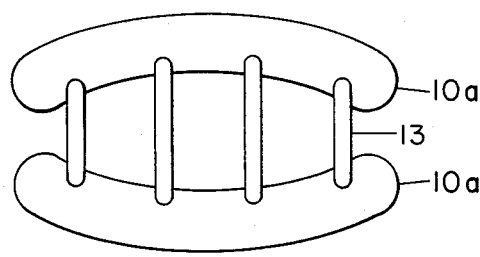
FIG. 2 is a top view of a second exemplary embodiment of the invention.

The construction of the device in FIG. 2 differs from that of FIG. 1 only in the use of strips 10a which are curved to approximate the contours of a user's lips.

Figure 3:
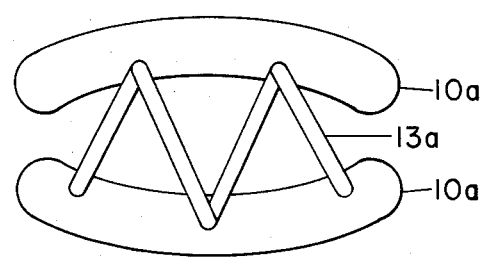
FIG. 3 is a top view of a third exemplary embodiment of the invention.

The construction of the device shown in FIG. 3 differs from that of FIG. 2 only in the use of connecting lines 13a which are connected diagonally between the strips. This configuration offers somewhat less inhibiting forces to the intake of food than the parallel lines, and may be preferable to some users.

Figure 4:
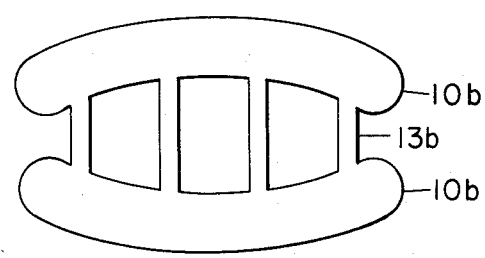
FIG. 4 is a top view of a fourth exemplary embodiment of the invention.

The construction of the device shown in FIG. 4 differs from the construction shown in FIG. 2 in that the connecting lines 13b are integral with the strips 10b. If the lines 13b are to be stretchable, then in this case, the strips 10b will also be stretchable.

Figure 5:
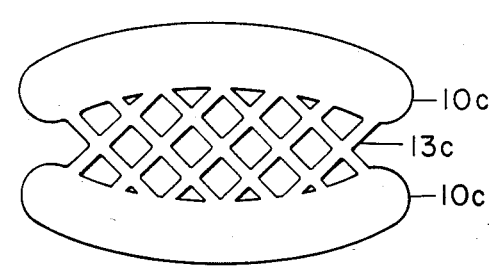
FIG. 5 is a top view of a fifth exemplary embodiment of the invention.

The construction of the device shown in FIG. 5 differs from the construction shown in FIG. 4 in that the connecting lines 13c which are integral with the strips 10c, are formed as a mesh. If the lines 13b are to be stretchable, then in this case as in the case for the embodiment of FIG. 4, the strips 10c will also be stretchable.

In each of the embodiments of the invention, I would propose, for cosmetic reasons, that the plastic strips be flesh tone, however, it may have some psychological advantages which I have not explored, to use bright colors or other decors.

THE USE OF THE INVENTION

To use the food intake control device, the dieter first peels off the protective covers 12, and then applies the strips 10 to just above and below the user's upper and lower lips. The ability of the user to open his lips and admit food is limited by the degree of elasticity in the connecting lines 13. Preferably, the elasticity of the lines 13 will permit the lines to stretch sufficiently to allow speech and the sipping of liquids through a straw, but will at least inhibit the wearer's intake of food. The degree of stretch in the lines can be controlled to some extent by the degree of initial stretch resulting from the positioning of the strips at the lips, that is, the initial distance between the parallel strips. This is a factor which each individual user will adjust for his or her own comfort. The devices are disposable after a single use. If the lines are not stretchable, then the ability for the user to open and close his mouth will be determined by the amount of slack left in the lines.

In summary, I have invented an appliance which will serve to help dieters with less than sufficient will power to control their eating habits, especially between meals, and to achieve the weight loss recommended for them.

Various modifications and adaptations will be apparent to persons skilled in the art, and it is intended, therefore, that this invention be limited only by the appended claims as interpretted in the light of the prior art. For example, in some instances it may be desirable that the lines be made from a materials such as fishing wire or dental floss, which are not materially stretchable, or with elastic band type materials which are stretchable.

I claim:

1. Apparatus for assisting in the reduction of food intake on the part of a person using the same, the combination comprising:
   first and second spaced parallel strips;

a plurality of lines interconnecting said strips;

a pressure sensitive adhesive on one side of said strips for securing said strips above and below the lips of a user, said lines bridging the lips of the user when the strips are secured, to thereby inhibit the normal intake of food while permitting speech and lip movement.

2. The invention as defined in claim 1, and a protective, peelable backing on said adhesive.

3. The invention as defined in claim 2 wherein said lines are elastic.

4. The invention as defined in claim 2 wherein said strips are contoured to approximate the shape of human lips.

5. The invention as defined in claim 2 wherein said lines are integral with said strips.

6. The invention as defined in claim 2 wherein said lines are at right approximate right angles to said strip.

7. The invention as defined in claim 2 wherein said lines are attached diagonally between said strips.

8. The invention as defined in claim 2 wherein said lines are in the form of a mesh extending between said strips.

* * * * *